United States Patent [19]

Wang et al.

[11] Patent Number: 6,124,485
[45] Date of Patent: Sep. 26, 2000

[54] PROCESS FOR PRODUCING 13-CIS RETINOIC ACID

[75] Inventors: Xiu C. Wang, Gurnee; Ashok V. Bhatia, Libertyville; Azad Hossain, Lindenhurst; Timothy B. Towne, Grayslake, all of Ill.

[73] Assignee: Abbott Laboratories, Abbott Park, Ill.

[21] Appl. No.: 09/047,700

[22] Filed: Mar. 25, 1998

[51] Int. Cl.$^7$ ................................. C07C 51/353
[52] U.S. Cl. .................. 554/125; 554/126; 554/129; 554/148
[58] Field of Search .................. 554/125, 126, 554/148, 129

[56] References Cited

U.S. PATENT DOCUMENTS

| 4,556,518 | 12/1985 | Lucci | 260/413 |
|---|---|---|---|
| 4,556,578 | 12/1985 | Meyer | 426/649 |
| 4,916,250 | 4/1990 | Babler | 558/217 |
| 5,061,819 | 10/1991 | Babler | 558/87 |
| 5,191,110 | 3/1993 | Solladie et al. | 560/260 |
| 5,424,465 | 6/1995 | John et al. | 554/125 |

FOREIGN PATENT DOCUMENTS

| 0111325 | 6/1984 | European Pat. Off. . |
|---|---|---|
| 0742204 | 11/1996 | European Pat. Off. . |
| 4313089 | 10/1994 | Germany . |

OTHER PUBLICATIONS

Tetrahedron Letters, 29(2):209–212 (1988).

*Primary Examiner*—Sreeni Padmanabhan
*Attorney, Agent, or Firm*—Lawrence S. Popo; Michael J. Ward

[57] ABSTRACT

The process of the present invention relates to a process for producing 1 3-cis retinoic acid. The process of the present invention involves reacting a Wittig salt in a solvent with a butenolide in the presence of a weak base and a Lewis acid.

8 Claims, No Drawings

PROCESS FOR PRODUCING 13-CIS RETINOIC ACID

TECHNICAL FIELD OF THE INVENTION

The present invention relates to a process for producing 13-cis retinoic acid.

BACKGROUND OF THE INVENTION

The 13-cis isomer of retinoic acid (2Z, 4E, 6E, 8E)-3,7-dimethyl-9(2,6,6-trimethylcyclohex-1-enyl)nona-2,4,6,8-tetraenoic acid, otherwise known as isotretinoin, is a valuable pharmaceutical that is used to treat acne. Many methods for synthesizing isotretinoin are known in the art. U.S. Pat. No. 4,556,518 (the '518 patent) describes a process for producing isotretinoin according to the following reaction scheme:

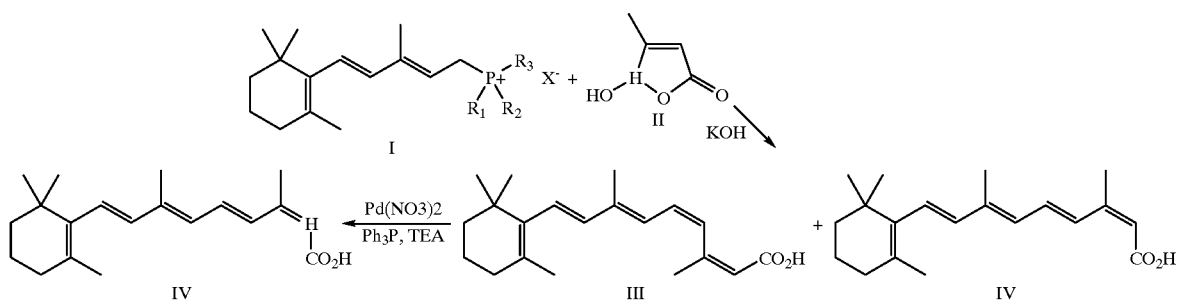

The first step of the reaction involves reacting a Wittig salt having the formula I with a butenolide having the formula II at a temperature of from about −10° to −50° C. in the presence of a strong base, such as a hydroxide or alkoxide, and an organic solvent. As shown above, the reaction of the Wittig salt having formula I and the butenolide of formula II produce compounds having the formula III and IV. The major product is the 11-cis isomer (formula III). In order to produce 13-cis retinoic acid as the major product, the compound having formula III is isomerized to produce a compound having formula IV. The isomerization reaction is carried out by treating the compound having formula III with a catalyst in an inert solvent medium. The catalyst is typically a compound or complex of palladium or rhodium. The catalyst selectively isomerizes the 11-cis double bond in the compound having formula III to the corresponding trans double bond without affecting the 13-cis double bond in order to produce a compound having the formula IV.

Therefore, there is a need in the art for a process of producing isotretinoin under moderate conditions that does not employ toxic heavy metals.

There are several difficulties associated with the reaction described in the '518 patent. First, palladium and rhodium are heavy metals which are toxic. It is also difficult to reduce the amounts of these heavy metals in the final product to an acceptable level. Moreover, the preferred temperature for the Wittig reaction is −25° C. or below which would necessitate the use of special equipment for commercial preparation.

U.S. Pat. No. 5,424,465 describes the use of irradiation in an organic solvent in the presence of a suitable photosensitizer to influence the isomerization of the 11-cis isomer to the 11-trans isomer. Disadvantages of this process include, having to recycle mother liquors to affect complete photoisomerization, the use of special equipment, and the removal of residual photosensitizer from the final product.

SUMMARY OF THE INVENTION

The present invention relates to a process for producing 13-cis retinoic acid, also known as isotretinoin. The process of the present invention involves reacting a Wittig salt in a solvent in the presence of a weak base and, optionally, a Lewis acid, with a butenolide via a Wittig reaction to produce 13-cis retinoic acid.

DETAILED DESCRIPTION OF THE INVENTION

The present invention involves a process for producing isotretinoin. Generally, the process of the present invention involves reacting a Wittig salt in a solvent, in the presence of a weak base and optionally, a Lewis acid, with a butenolide via a Wittig reaction, to produce isotretinoin. The isotretinoin prepared according to the process of the present invention is produced directly from the Wittig reaction. The process of the present invention is shown in Scheme I.

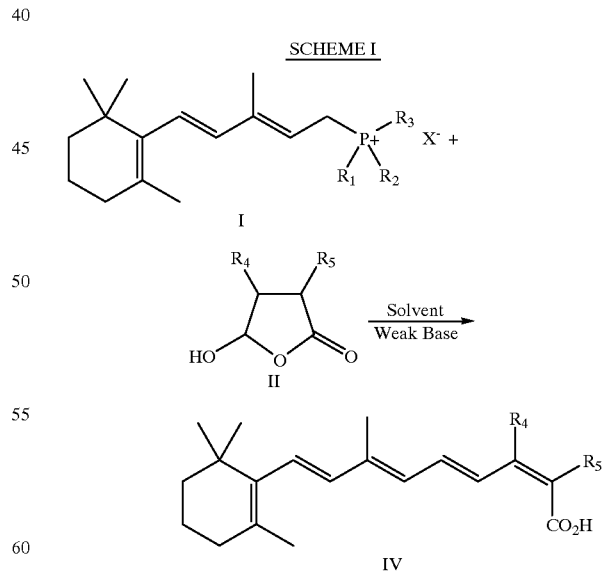

The process of the present invention employs a Wittig salt of the formula I

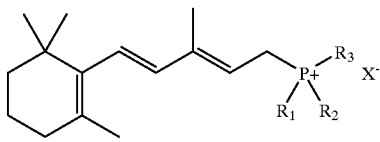

wherein $R^1$, $R^2$ and $R^3$ are aryl or dialkylamino, and X is halogen or hydrogen sulfate.

For the purposes of this disclosure, the above terms have the following meanings:

The terms "loweralkyl" or "alkyl" as used herein refer to straight or branched chain alkyl radicals containing from 1 to 6 carbon atoms including, but not limited to, methyl, ethyl, n-propyl, iso-propyl, n-butyl, iso-butyl, sec-butyl, t-butyl, n-pentyl, 1-methylbutyl, 2,2-dimethylbutyl, 2-methylpentyl, 2,2-dimethylpropyl, n-hexyl and the like.

The term "dialkylamino" as used herein refers to $R_{11}R_{12}N$— wherein $R_{11}$ and $R_{12}$ are independently selected from loweralkyl, for example diethylamino, methyl propylamino, and the like.

As used herein, the term "aryl" refers to a mono- or bicyclic carbocyclic ring system having one or two aromatic rings including, but not limited to, phenyl, naphthyl, anthryl, phenanthryl, tetrahydronaphthyl, indanyl, indenyl and the like. Aryl groups can be unsubstituted or substituted with one, two or three substituents independently selected from loweralkyl, halogen, haloalkyl, hydroxy, hydroxyalkyl, alkenyl, alkenyloxy, alkoxy, alkoxyalkoxy, alkoxycarbonyl, amino, alkylamino, alkylsulfonyl, dialkylamino, aminocarbonyl, aminocarbonylalkoxy, aryl, arylalkyl, arylalkoxy, aryloxy, cyano, nitro, carboxy, cycloalkyl, cycloalkylalkyl, carboxyalkoxy, alkylsulfonylamino, and phenyl. Examples of substituted aryl include 3-chlorophenyl, 3-fluorophenyl, 4-chlorophenyl, 4-fluorophenyl, 3,4-dichlorophenyl, 3-chloro-4-fluorophenyl, 4-methylsulfonylphenyl, 4-isopropoxyphenyl, and the like.

The term "alkoxy" as used herein refers to $R_{13}O$— wherein $R_{13}$ is a loweralkyl group, as defined above. Examples of alkoxy include, but are not limited to, ethoxy, tert-butoxy, and the like.

The term "cycloalkyl" as used herein refers to an aliphatic ring system having 3 to 10 carbon atoms and 1 to 3 rings including, but not limited to, cyclopropyl, cyclopentyl, cyclohexyl, norbornyl, adamantyl, and the like. Cycloalkyl groups can be unsubstituted or substituted with one, two or three substituents independently selected from loweralkyl, haloalkyl, alkoxy, thioalkoxy, amino, alkylamino, dialkylamino, hydroxy, halo, mercapto, nitro, carboxaldehyde, carboxy, alkoxycarbonyl and carboxamide.

The term "halogen" or "halo" refers to one of the electronegative elements of group VIIA of the periodic table, such as fluorine, chlorine, bromine, iodine and astatine.

The terms "heterocyclic ring" or "heterocyclic" or "heterocycle" as used herein refers to any 3- or 4-membered ring containing a heteroatom selected from oxygen, nitrogen and sulfur; or a 5-, 6- or 7-membered ring containing one, two or three nitrogen atoms; one nitrogen and one sulfur atom; or one nitrogen and one oxygen atom. The 5-membered ring has 0–2 double bonds and the 6- and 7-membered ring have 0–3 double bonds. The nitrogen heteroatoms can be optionally quaternized. The term "heterocyclic" also includes bicyclic groups in which any of the above heterocyclic rings is fused to a benzene ring or a cyclohexane ring or another heterocyclic ring (for example, indolyl, quinolyl, isoquinolyl, tetrahydroquinolyl, benzofuryl or benzothienyl and the like). Heterocyclics include: azetidinyl, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl and benzothienyl.

Heterocyclics can be unsubstituted or monosubstituted or disubstituted with substituents independently selected from hydroxy, halo, oxo (=O), alkylimino (R*N= wherein R* is a loweralkyl group), amino, alkylamino, dialkylamino, alkoxy, alkoxyalkoxy, haloalkyl, cycloalkyl, aryl, arylalkyl, —COOH, —SO₃H and loweralkyl. In addition, nitrogen containing heterocycles can be N-protected.

The compound of formula I can be any conventional Wittig salt. Preferably, the compound of formula I is a triphenyl phosphonium chloride or bromide salt.

The Wittig salt having formula I can be prepared by any method known in the art. For example, the Wittig salt can be prepared by reacting vinyl-β-ionol with triphenylphosphine hydrobromide to give a triphenyl phosphonium bromide salt having the formula I. This triphenyl phosphonium bromide salt can be used directly after solvent evaporation to prepare isotretinoin. An advantage of the process is that the Wittig salt does not have to be isolated for use. The remaining ingredients required for the synthesis of isotretinoin can be added directly to the reaction vessel used for the synthesis of the Wittig salt.

After a Wittig salt having formula I is prepared, the Wittig salt is dissolved in a solvent to form a reaction mixture. Preferably, the solvent is a polar aprotic solvent. Any polar aprotic solvent or mixture of polar aprotic solvents can be used in the process of the present invention. Examples of polar aprotic solvents that can be used in the process of the present invention include, but are not intended to be limited to, methylene chloride, chloroform, acetonitrile, tetrahydrofuran, 1,4-dioxane, N,N'-dimethylformamide, 1-methyl-2-pyrrolidinone, 1,3-dimethyl-2-imidazolidinone, N,N'-dimethylacetamide, and mixtures thereof. Additionally, the solvent can be a mixture of a polar aprotic solvent and a non-polar solvent. Examples of non-polar solvents that can be used in the process of the present invention include, but are not intended to be limited to, toluene and chlorobenzene.

In accordance with the process of the present invention, the Wittig salt of formula I is reacted in a solvent in the presence of a weak base and optionally, a Lewis acid, with a butenolide having the formula II:

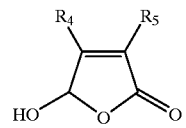

wherein $R_4$ and $R_5$ are independently hydrogen, loweralkyl, alkoxy, cycloalkyl, aryl, or heterocyclic. In the process of making isotretinoin (formula IV), $R_4$ is methyl and $R_5$ is hydrogen:

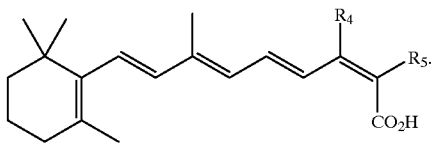

The order of addition of the weak base, Lewis acid and butenolide to the reaction mixture is not critical. In carrying out the reaction of the present invention, one may use an inert atmosphere, such as nitrogen, to prevent oxidation of the end product.

The molar ratio of butenolide to the Wittig salt in the reaction mixture is from about 1:1 to about 10:1, preferably from about 1:1 to about 2:1.

Any weak base can be used in the process of the present invention. As used herein, the term "weak base" means a base that has a low percentage ionization in solution. Examples of weak bases that can be used in the present invention include, but are not intended to be limited to, tertiary amines such as triethylamine, diisopropylethylamine, and N-ethylpiperidine, carbonates, bicarbonates, and acetates of sodium, potassium or cesium. The molar ratio of weak base to butenolide in the reaction mixture is from about 2:1 to about 10:1, preferably from about 3:1 to about 7:1.

A Lewis acid can be optionally employed in the process of the present invention. As used herein, the term "Lewis acid" refers to any molecule or ion (called an electrophile) that can combine with another molecule or ion by forming a bond with two electrons to form a second molecule or ion. Examples of suitable Lewis acids that can be used in the present invention include, but are not intended to be limited to, magnesium chloride, magnesium triflate, magnesium bromide, magnesium trifluroacetate, magnesium iodide, and magnesium fluoride. If a Lewis acid is used in the process of the present invention, it is preferred that prior to the addition of the Lewis acid that the reaction mixture be cooled to a temperature of from about −5° C. to about 15° C. The molar ratio of Lewis acid to Wittig salt having formula I in the reaction mixture is from about 1:1 to about 3:1, preferably from about 1.5:1 to about 2.5:1.

After the butenolide, weak base and optionally, the Lewis acid, are added to the reaction mixture, the reaction mixture is stirred at ambient temperature under an inert atmosphere for a period of time of from about 10 hours to about 72 hours, preferably from about 15 hours to about 48 hours. After stirring, the isotretinoin is recovered from the reaction mixture using techniques well known in the art.

Utilizing conventional conditions of a Wittig reaction, the major product produced is the 11-cis isomer of isotretinoin. In the process of the present invention, the stereoselectivity of a conventional Wittig reaction is reversed by reacting the Wittig salt with the butenolide in presence of a weak base to preferentially produce isotretinoin. The amount of isotretinoin recovered in the reaction may be increased if a Lewis acid is used in the reaction mixture with the weak base.

In a preferred embodiment of the present invention, butenolide and a weak base are added to the reaction mixture containing the Wittig salt dissolved in a polar aprotic solvent. The resulting suspension is cooled to 0° C., followed by the addition of a Lewis acid. The reaction mixture is stirred for about 15 hours at ambient temperature. Isotretinoin is then recovered from the reaction mixture. Because the process of the present invention does not employ any heavy metals or photosensitizer, the quality of the isotretinoin produced as a result of the process is improved.

The following Example illustrates the preferred embodiment of the process of the present invention and is not limiting of the specification and claims in any way.

EXAMPLE 1

Preparation of Isotretinoin

Synthesis of Isotretinoin Using Triethylamine and Magnesium Chloride

N,N-dimethylacetamide (300 milliliters (mL)), 5-hydroxy-4-methyl-2[5H]-furanone (26.81 grams (g)), 235 millimoles (mmol), 1.2 equivalents), and triethylamine (164 mL, 1.2 moles, 6 equivalents) were added to 107.26 g (197 mmol) of [3-methyl-5-(2,6,6-trimethyl-1-cyclohexen-1-yl)-2,4-pentadienyl] triphenyl phosphonium salt. The resulting mixture was cooled to 15° C. prior to addition of magnesium chloride (30.03 g, 315 mmol, 1.6 equivalents). The reaction mixture was allowed to stir at room temperature for 17 hours. The reaction solution was washed with 200 mL of heptane. Toluene (100 mL) was added and the solution was acidified with 280 mL of 20% by volume HCl. The aqueous layer was back-extracted three times, each time with 200 mL of a 9:1 heptane:toluene mixture. The combined organic layers were washed with aqueous methanol, water, and then concentrated to give an orange solid. Heptane (250 mL) was added to the crude solid and the slurry was cooled to 0° C. and then filtered. Acetone (200 mL) and heptane (800 mL) were added to the solid and the resulting mixture was stirred at 25° C. Filtration of this slurry provided isotretinoin with >98% purity as a solid. $^1$H NMR: (300 MHz, CDCl$_3$):δ 1.03(s,6; H), 1.44–1.68(m,4H), 1.72(s,3H), 1.88–2.05(m, 2H), 2.0(s,3H), 2.11 (d,3H), 5.67(s,1H), 6.15–6.32(m,3H), 7.03 (dd,1H), 7.76 (d,1H).

What is claimed is:

1. A process for producing a compound of formula IV:

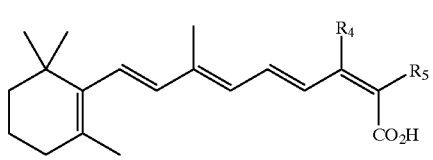

comprising the steps of reacting in a solvent consisting of a mixture of a polar aprotic solvent and a non-polar solvent, in the presence of a weak base and a Lewis acid, a butenolide of the formula II:

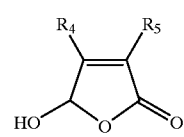

with a salt of the formula I:

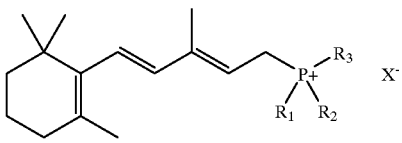

wherein $R_1$, $R_2$, $R_3$ are independently selected from aryl or dialkylamino, and $R_4$ and $R_5$ are independently selected from hydrogen, loweralkyl, alkoxy, cycloalkyl, aryl or heterocyclyl, and X is selected from halogen or hydrogen sulfate.

2. The process of claim 1 wherein the Lewis acid is magnesium triflate, magnesium bromide, magnesium trifluoracetate, magnesium chloride, magnesium iodide or magnesium fluoride.

3. The process of claim 1 wherein the molar ratio of Lewis acid to the Wittig salt is from about 1:1 to about 3:1.

4. The process of claim 1 wherein the ratio of weak base to butenolide is from about 2:1 to about 10:1.

5. The process of claim 1 wherein the ratio of butenolide to the Wittig salt is from about 1:1 to about 10:1.

6. The process of claim 1 wherein said compound is 13-cis retinoic acid.

7. The process of claim 1 wherein the weak base is a tertiary amine.

8. The process of claim 7 wherein said tertiary amine is selected from triethylamine, diisopropylethylamine, and N-ethylpiperidine.

* * * * *

UNITED STATES PATENT AND TRADEMARK OFFICE
CERTIFICATE OF CORRECTION

PATENT NO.    : 6,124,485  
DATED         : September 26, 2000  
INVENTOR(S)   : Xiu C. Wang et al.

It is certified that error appears in the above-identified patent and that said Letters Patent is hereby corrected as shown below:

<u>Title page,</u>  
Item [57], ABSTRACT,  
Replace "presence of a weak base and a lewis acid." with -- presence of a weak base and optionally, a lewis acid. --.

Signed and Sealed this

Twenty-sixth Day of February, 2002

Attest:

Attesting Officer

JAMES E. ROGAN  
*Director of the United States Patent and Trademark Office*